(12) United States Patent
Zentgraf et al.

(10) Patent No.: US 10,080,659 B1
(45) Date of Patent: Sep. 25, 2018

(54) DEVICES AND METHODS FOR MINIMALLY INVASIVE REPAIR OF HEART VALVES

(75) Inventors: John Zentgraf, Minneapolis, MN (US); David Joseph Parins, Corcoran, MN (US); Arun Sarini, Burnsville, MN (US); Giovanni Speziali, Pittsburgh, PA (US)

(73) Assignee: NeoChord, Inc., St. Louis Park, MN (US)

( * ) Notice: Subject to any disclaimer, the term of this patent is extended or adjusted under 35 U.S.C. 154(b) by 246 days.

(21) Appl. No.: 13/340,185

(22) Filed: Dec. 29, 2011

Related U.S. Application Data

(60) Provisional application No. 61/428,048, filed on Dec. 29, 2010.

(51) Int. Cl.
*A61F 2/24* (2006.01)

(52) U.S. Cl.
CPC .......... *A61F 2/2445* (2013.01); *A61F 2/2457* (2013.01)

(58) Field of Classification Search
CPC ................ A61F 2/24; A61F 2/2427; A61F 2/243–2/2469
USPC ................ 623/1.24, 1.26, 2.1–2.42
See application file for complete search history.

(56) References Cited

U.S. PATENT DOCUMENTS

| | | |
|---|---|---|
| 2,751,908 A | 6/1956 | Wallace |
| 3,667,474 A | 6/1972 | Lapkin |
| 3,744,062 A * | 7/1973 | Parsonnet ............ 623/2.19 |
| 3,842,840 A | 10/1974 | Schweizer |
| 4,258,716 A | 3/1981 | Sutherland |
| 4,351,345 A | 9/1982 | Carney |
| 4,935,027 A | 6/1990 | Yoon |
| 4,957,498 A | 9/1990 | Caspari et al. |
| 4,960,424 A | 10/1990 | Grooters |
| 4,967,498 A | 11/1990 | Kao |
| 4,967,798 A | 11/1990 | Hammer |
| 4,972,874 A | 11/1990 | Jackson |
| 5,053,013 A | 10/1991 | Ensminger |
| 5,059,201 A | 10/1991 | Asnis |
| 5,211,650 A | 5/1993 | Noda |
| 5,297,536 A | 3/1994 | Wilk |
| 5,304,185 A | 4/1994 | Taylor |

(Continued)

FOREIGN PATENT DOCUMENTS

| | | |
|---|---|---|
| DE | 20 2004 01788 U1 | 5/2005 |
| EP | 1039851 B1 | 7/2005 |

(Continued)

OTHER PUBLICATIONS

US 6,197,052, 03/2001, Cosgrove (withdrawn)

(Continued)

*Primary Examiner* — Darwin Erezo
*Assistant Examiner* — Jonathan Hollm
(74) *Attorney, Agent, or Firm* — Patterson Thuente Pedersen, P.A.

(57) ABSTRACT

Methods and apparatus for heart valve repair utilize a heart valve repair device including a generally annular ring-like structure and a net structure. The ring-like structure is seated in the valve annulus with the net structure extending from the ring-like structure through the coaptation zone between leaflets. The net structure can then be anchored to a heart structure with a suture. Net structure extending between leaflets helps prevent prolapse of leaflets and can aid in coaptation.

16 Claims, 14 Drawing Sheets

(56) References Cited

U.S. PATENT DOCUMENTS

| | | |
|---|---|---|
| 5,312,423 A | 5/1994 | Rosenbluth |
| 5,336,229 A | 8/1994 | Noda |
| 5,383,877 A | 1/1995 | Clarke |
| 5,433,723 A | 7/1995 | Lindenberg et al. |
| 5,452,733 A | 9/1995 | Sterman |
| 5,474,519 A | 12/1995 | Bloomer |
| 5,547,455 A | 8/1996 | McKenna |
| 5,556,411 A | 9/1996 | Taoda |
| 5,571,215 A | 11/1996 | Sterman |
| 5,601,578 A | 2/1997 | Murphy |
| 5,626,607 A | 5/1997 | Malecki |
| 5,653,716 A | 8/1997 | Malo |
| 5,665,100 A | 9/1997 | Yoon |
| 5,667,472 A | 9/1997 | Finn |
| 5,667,473 A | 9/1997 | Finn |
| 5,667,478 A | 9/1997 | McFarlin |
| 5,693,091 A | 12/1997 | Larson |
| 5,728,113 A | 3/1998 | Sherts |
| 5,762,458 A | 6/1998 | Wang |
| 5,762,613 A | 6/1998 | Sutton |
| 5,766,163 A | 6/1998 | Mueller |
| 5,772,597 A | 6/1998 | Goldberger |
| 5,772,672 A | 6/1998 | Toy |
| 5,785,658 A | 7/1998 | Benaron |
| 5,797,960 A | 8/1998 | Stevens |
| 5,830,231 A | 11/1998 | Geiges |
| 5,839,639 A | 11/1998 | Sauer |
| 5,897,564 A | 4/1999 | Schulze |
| 5,908,428 A | 6/1999 | Scirica |
| 5,908,429 A | 6/1999 | Yoon |
| 5,919,128 A | 7/1999 | Fitch |
| 5,961,440 A | 10/1999 | Schweich |
| 5,972,004 A | 10/1999 | Williamson |
| 5,972,030 A | 10/1999 | Garrison |
| 5,984,939 A | 11/1999 | Yoon |
| 5,993,466 A | 11/1999 | Yoon |
| 5,993,467 A | 11/1999 | Yoon |
| 6,022,360 A | 2/2000 | Reimels |
| 6,045,497 A | 4/2000 | Schweich |
| 6,050,936 A | 4/2000 | Schweich |
| 6,053,933 A | 4/2000 | Balazs |
| 6,059,715 A | 5/2000 | Schweich |
| 6,077,214 A | 6/2000 | Mortier |
| 6,117,144 A | 9/2000 | Nobles |
| 6,129,683 A | 10/2000 | Sutton |
| 6,149,660 A | 11/2000 | Laufer |
| 6,152,934 A | 11/2000 | Harper |
| 6,162,168 A | 12/2000 | Schweich |
| 6,162,233 A | 12/2000 | Williamson |
| 6,165,119 A | 12/2000 | Schweich |
| 6,165,120 A | 12/2000 | Schweich |
| 6,165,183 A | 12/2000 | Kuehn |
| 6,178,346 B1 | 1/2001 | Amundson |
| 6,183,411 B1 | 2/2001 | Mortier |
| 6,190,357 B1 | 2/2001 | Ferrari |
| 6,234,079 B1 | 5/2001 | Chertkow |
| 6,234,995 B1 | 5/2001 | Peacock |
| 6,245,079 B1 | 6/2001 | Nobles |
| 6,260,552 B1 | 7/2001 | Mortier |
| 6,261,222 B1 | 7/2001 | Schweich |
| 6,264,602 B1 | 7/2001 | Mortier |
| 6,269,819 B1 | 8/2001 | Oz |
| 6,270,508 B1 | 8/2001 | Klieman |
| 6,283,993 B1 | 9/2001 | Cosgrove |
| 6,312,447 B1 | 11/2001 | Grimes |
| 6,332,863 B1 | 12/2001 | Schweich |
| 6,332,864 B1 | 12/2001 | Schweich |
| 6,332,893 B1 | 12/2001 | Mortier |
| 6,355,050 B1 | 3/2002 | Andreas |
| 6,401,720 B1 | 6/2002 | Stevens |
| 6,402,679 B1 | 6/2002 | Mortier |
| 6,402,680 B2 | 6/2002 | Mortier |
| 6,402,781 B1 | 6/2002 | Langberg |
| 6,406,420 B1 | 6/2002 | McCarthy |
| 6,419,626 B1 | 7/2002 | Yoon |
| 6,436,107 B1 | 8/2002 | Wang |
| 6,443,922 B1 | 9/2002 | Roberts |
| 6,451,054 B1 | 9/2002 | Stevens |
| 6,461,366 B1 | 10/2002 | Seguin |
| 6,508,777 B1 | 1/2003 | Macoviak |
| 6,514,194 B2 | 2/2003 | Schweich |
| 6,533,796 B1 | 3/2003 | Sauer |
| 6,537,198 B1 | 3/2003 | Vidlund |
| 6,537,314 B2 | 3/2003 | Langberg |
| 6,551,331 B2 | 4/2003 | Nobles |
| 6,558,416 B2 | 5/2003 | Cosgrove |
| 6,562,052 B2 | 5/2003 | Nobles |
| 6,564,805 B2 | 5/2003 | Garrison |
| 6,582,388 B1 | 6/2003 | Kadan |
| 6,585,727 B1 | 7/2003 | Cashman |
| 6,589,160 B2 | 7/2003 | Schweich |
| 6,602,288 B1 | 8/2003 | Cosgrove |
| 6,616,684 B1 | 9/2003 | Vidlund |
| 6,619,291 B2 | 9/2003 | Hlavka |
| 6,622,730 B2 | 9/2003 | Ekvall |
| 6,626,917 B1 | 9/2003 | Craig |
| 6,626,930 B1 | 9/2003 | Allen |
| 6,629,534 B1 | 10/2003 | Dell |
| 6,629,921 B1 | 10/2003 | Schweich |
| 6,629,984 B1 | 10/2003 | Chan |
| 6,645,205 B2 | 11/2003 | Ginn |
| 6,679,268 B2 | 1/2004 | Stevens |
| 6,692,605 B2 | 2/2004 | Kerr et al. |
| 6,695,866 B1 | 2/2004 | Kuehn |
| 6,709,456 B2 | 3/2004 | Langberg |
| 6,718,985 B2 | 4/2004 | Hlavka |
| 6,723,038 B1 | 4/2004 | Schroeder |
| 6,726,648 B2 | 4/2004 | Kaplon et al. |
| 6,733,509 B2 | 5/2004 | Nobles |
| 6,740,107 B2 | 5/2004 | Graham |
| 6,746,471 B2 | 6/2004 | Mortier |
| 6,752,713 B2 | 6/2004 | Johnson |
| 6,752,813 B2 | 6/2004 | Goldfarb |
| 6,755,777 B2 | 6/2004 | Schweich |
| 6,764,510 B2 | 7/2004 | Vidlund |
| 6,770,083 B2 | 8/2004 | Seguin |
| 6,770,084 B1 | 8/2004 | Bain |
| 6,793,618 B2 | 9/2004 | Schweich |
| 6,802,860 B2 | 10/2004 | Cosgrove |
| 6,808,488 B2 | 10/2004 | Mortier |
| 6,810,882 B2 | 11/2004 | Langberg |
| 6,840,246 B2 | 1/2005 | Downing |
| 6,858,003 B2 | 2/2005 | Evans |
| 6,875,224 B2 | 4/2005 | Grimes |
| 6,893,448 B2 | 5/2005 | O'Quinn |
| 6,908,424 B2 | 6/2005 | Mortier |
| 6,918,917 B1 | 7/2005 | Nguyen |
| 6,921,407 B2 | 7/2005 | Nguyen |
| 6,929,715 B2 | 8/2005 | Fladda |
| 6,936,054 B2 | 8/2005 | Chu |
| 6,955,175 B2 | 10/2005 | Stevens |
| 6,962,605 B2 | 11/2005 | Cosgrove |
| 6,978,176 B2 | 12/2005 | Lattouf |
| 6,986,775 B2 | 1/2006 | Morales |
| 6,989,028 B2 | 1/2006 | Lashinski |
| 6,991,635 B2 | 1/2006 | Takamoto |
| 6,997,950 B2 | 2/2006 | Chawla |
| 7,004,176 B2 | 2/2006 | Lau |
| 7,004,952 B2 | 2/2006 | Nobles |
| 7,011,669 B2 | 3/2006 | Kimblad |
| 7,044,905 B2 | 5/2006 | Vidlund |
| 7,048,754 B2 | 5/2006 | Martin |
| 7,077,862 B2 | 7/2006 | Vidlund |
| 7,083,628 B2 | 8/2006 | Bachman |
| 7,083,638 B2 | 8/2006 | Foerster |
| 7,090,686 B2 | 8/2006 | Nobles |
| 7,094,244 B2 | 8/2006 | Schreck |
| 7,100,614 B2 | 9/2006 | Stevens |
| 7,112,207 B2 | 9/2006 | Allen |
| 7,112,219 B2 | 9/2006 | Vidlund |
| 7,118,583 B2 | 10/2006 | O'Quinn |
| 7,122,040 B2 | 10/2006 | Hill |
| 7,179,291 B2 | 2/2007 | Rourke |
| 7,186,264 B2 | 3/2007 | Liddicoat |

(56) References Cited

U.S. PATENT DOCUMENTS

| | | |
|---|---|---|
| 7,189,199 B2 | 3/2007 | McCarthy |
| 7,217,240 B2 | 5/2007 | Snow |
| 7,226,467 B2 | 6/2007 | Lucatero |
| 7,247,134 B2 | 7/2007 | Vidlund |
| 7,250,028 B2 | 7/2007 | Julian |
| 7,288,097 B2 | 10/2007 | Seguin |
| 7,294,148 B2 | 11/2007 | McCarthy |
| 7,381,210 B2 | 6/2008 | Zarbatany |
| 7,464,712 B2 | 12/2008 | Oz |
| 7,563,267 B2 | 7/2009 | Goldfarb |
| 7,563,273 B2 | 7/2009 | Goldfarb |
| 7,604,646 B2 | 10/2009 | Goldfarb |
| 7,608,091 B2 | 10/2009 | Goldfarb |
| 7,635,386 B1 | 12/2009 | Gammie |
| 7,666,204 B2 | 2/2010 | Thornton |
| 7,815,654 B2 | 10/2010 | Chu |
| 7,879,048 B2 | 2/2011 | Bain |
| 7,887,552 B2 | 2/2011 | Bachman |
| 8,052,751 B2 | 11/2011 | Aklog et al. |
| 8,465,500 B2 | 6/2013 | Speziali |
| 8,758,393 B2 | 6/2014 | Zentgraf |
| 9,044,221 B2 | 6/2015 | Zentgraf et al. |
| 2001/0005787 A1 | 6/2001 | Oz |
| 2001/0016675 A1 | 8/2001 | Mortier |
| 2001/0021872 A1 | 9/2001 | Bailey |
| 2002/0013571 A1 | 1/2002 | Goldfarb |
| 2002/0029080 A1 | 3/2002 | Mortier |
| 2002/0049402 A1 | 4/2002 | Peacock |
| 2002/0077524 A1 | 6/2002 | Schweich |
| 2002/0169359 A1 | 11/2002 | McCarthy |
| 2002/0173694 A1 | 11/2002 | Mortier |
| 2002/0183766 A1 | 12/2002 | Seguin |
| 2003/0004562 A1 | 1/2003 | DiCarlo |
| 2003/0032979 A1 | 2/2003 | Mortier |
| 2003/0050529 A1 | 3/2003 | Vidlund |
| 2003/0050693 A1 | 3/2003 | Quijano |
| 2003/0078600 A1 | 4/2003 | O'Quinn |
| 2003/0105519 A1 | 6/2003 | Fasol |
| 2003/0130731 A1 | 7/2003 | Vidlund |
| 2003/0166992 A1 | 9/2003 | Schweich |
| 2003/0167071 A1 | 9/2003 | Martin |
| 2003/0171641 A1 | 9/2003 | Schweich |
| 2003/0181928 A1 | 9/2003 | Vidlund |
| 2003/0187457 A1 | 10/2003 | Weber |
| 2003/0195529 A1 | 10/2003 | Takamoto |
| 2003/0199975 A1* | 10/2003 | Gabbay ............ 623/2.36 |
| 2004/0003819 A1 | 1/2004 | St. Goar |
| 2004/0030382 A1 | 2/2004 | St. Goar |
| 2004/0039442 A1 | 2/2004 | St. Goar |
| 2004/0044350 A1 | 3/2004 | Martin |
| 2004/0044365 A1 | 3/2004 | Bachman |
| 2004/0049207 A1 | 3/2004 | Goldfarb |
| 2004/0049552 A1 | 3/2004 | Motoyama |
| 2004/0087975 A1 | 5/2004 | Lucatero |
| 2004/0087978 A1 | 5/2004 | Velez et al. |
| 2004/0092962 A1 | 5/2004 | Thornton |
| 2004/0097805 A1 | 5/2004 | Verard |
| 2004/0116767 A1 | 6/2004 | Lebovic |
| 2004/0122448 A1 | 6/2004 | Levine |
| 2004/0127983 A1 | 7/2004 | Mortier |
| 2004/0133063 A1 | 7/2004 | McCarthy |
| 2004/0167374 A1 | 8/2004 | Schweich |
| 2004/0167539 A1 | 8/2004 | Kuehn |
| 2004/0220593 A1* | 11/2004 | Greenhalgh ............ 606/151 |
| 2004/0225300 A1 | 11/2004 | Goldfarb |
| 2004/0225304 A1 | 11/2004 | Vidlund |
| 2004/0236353 A1 | 11/2004 | Bain |
| 2004/0236354 A1 | 11/2004 | Seguin |
| 2004/0243229 A1 | 12/2004 | Vidlund |
| 2004/0267083 A1 | 12/2004 | McCarthy |
| 2005/0004665 A1 | 1/2005 | Aklog et al. |
| 2005/0004668 A1* | 1/2005 | Aklog ............ A61F 2/2448 623/2.36 |
| 2005/0021055 A1 | 1/2005 | Toubia |
| 2005/0021056 A1 | 1/2005 | St. Goar |
| 2005/0021057 A1 | 1/2005 | St. Goar |
| 2005/0033446 A1 | 2/2005 | Deem |
| 2005/0044365 A1 | 2/2005 | Bachman |
| 2005/0049667 A1 | 3/2005 | Arbefeuille et al. |
| 2005/0065396 A1 | 3/2005 | Mortier |
| 2005/0075723 A1 | 4/2005 | Schroeder |
| 2005/0075727 A1* | 4/2005 | Wheatley ............ 623/2.17 |
| 2005/0101975 A1 | 5/2005 | Nguyen |
| 2005/0125011 A1 | 6/2005 | Spence |
| 2005/0131277 A1 | 6/2005 | Schweich |
| 2005/0131533 A1 | 6/2005 | Alfieri |
| 2005/0143620 A1 | 6/2005 | Mortier |
| 2005/0148815 A1 | 7/2005 | Mortier |
| 2005/0149014 A1 | 7/2005 | Hauck |
| 2005/0154402 A1 | 7/2005 | Sauer |
| 2005/0165419 A1 | 7/2005 | Sauer |
| 2005/0171601 A1 | 8/2005 | Cosgrove |
| 2005/0216039 A1 | 9/2005 | Lederman |
| 2005/0240202 A1 | 10/2005 | Shennib |
| 2005/0251187 A1 | 11/2005 | Beane |
| 2006/0020275 A1 | 1/2006 | Goldfarb et al. |
| 2006/0036317 A1 | 2/2006 | Vidlund |
| 2006/0041306 A1 | 2/2006 | Vidlund |
| 2006/0052868 A1 | 3/2006 | Mortier |
| 2006/0058871 A1 | 3/2006 | Zakay |
| 2006/0074484 A1 | 4/2006 | Huber |
| 2006/0074485 A1 | 4/2006 | Realyvasquez |
| 2006/0089671 A1 | 4/2006 | Goldfarb |
| 2006/0100699 A1 | 5/2006 | Vidlund |
| 2006/0127509 A1 | 6/2006 | Eckman |
| 2006/0135993 A1 | 6/2006 | Seguin |
| 2006/0149123 A1 | 7/2006 | Vidlund |
| 2006/0161040 A1 | 7/2006 | McCarthy |
| 2006/0161193 A1 | 7/2006 | Beane |
| 2006/0184203 A1 | 8/2006 | Martin |
| 2006/0195012 A1 | 8/2006 | Mortier |
| 2006/0195134 A1 | 8/2006 | Crittenden |
| 2006/0195183 A1* | 8/2006 | Navia et al. ............ 623/2.18 |
| 2006/0241340 A1 | 10/2006 | Schroeder |
| 2006/0287657 A1 | 12/2006 | Bachman |
| 2007/0002627 A1 | 1/2007 | Youn |
| 2007/0027451 A1 | 2/2007 | Desinger |
| 2007/0049952 A1 | 3/2007 | Weiss |
| 2007/0050022 A1 | 3/2007 | Vidlund |
| 2007/0055303 A1 | 3/2007 | Vidlund |
| 2007/0088375 A1 | 4/2007 | Beane |
| 2007/0100356 A1 | 5/2007 | Lucatero |
| 2007/0112244 A1 | 5/2007 | McCarthy |
| 2007/0118154 A1 | 5/2007 | Crabtree |
| 2007/0118155 A1 | 5/2007 | Goldfarb |
| 2007/0129737 A1 | 6/2007 | Goldfarb |
| 2007/0179511 A1 | 8/2007 | Paolitto |
| 2007/0197858 A1 | 8/2007 | Goldfarb |
| 2007/0203391 A1 | 8/2007 | Bloom |
| 2007/0232941 A1 | 10/2007 | Rabinovich |
| 2007/0239272 A1 | 10/2007 | Navia |
| 2007/0265643 A1 | 11/2007 | Beane |
| 2007/0299468 A1 | 12/2007 | Viola |
| 2008/0027468 A1 | 1/2008 | Fenton |
| 2008/0051703 A1 | 2/2008 | Thornton |
| 2008/0065011 A1 | 3/2008 | Marchand |
| 2008/0065156 A1 | 3/2008 | Hauser |
| 2008/0065205 A1 | 3/2008 | Nguyen |
| 2008/0091059 A1 | 4/2008 | Machold |
| 2008/0091264 A1 | 4/2008 | Machold |
| 2008/0097482 A1 | 4/2008 | Bain et al. |
| 2008/0097489 A1 | 4/2008 | Goldfarb |
| 2008/0167714 A1 | 7/2008 | St. Goar |
| 2008/0183194 A1 | 7/2008 | Goldfarb |
| 2008/0188873 A1 | 8/2008 | Speziali |
| 2008/0195200 A1 | 8/2008 | Vidlund |
| 2008/0208006 A1 | 8/2008 | Farr |
| 2008/0228223 A1 | 9/2008 | Alkhatib |
| 2009/0082857 A1* | 3/2009 | Lashinski et al. ............ 623/2.18 |
| 2009/0105729 A1 | 4/2009 | Zentgraf |
| 2009/0105751 A1 | 4/2009 | Zentgraf |
| 2009/0131880 A1 | 5/2009 | Speziali |
| 2009/0156995 A1 | 6/2009 | Martin |
| 2009/0163934 A1 | 6/2009 | Raschdorf |

(56) References Cited

U.S. PATENT DOCUMENTS

| | | | |
|---|---|---|---|
| 2009/0177274 A1* | 7/2009 | Scorsin et al. | 623/2.1 |
| 2009/0259304 A1 | 10/2009 | O'Beirne | |
| 2010/0042147 A1* | 2/2010 | Janovsky et al. | 606/228 |
| 2010/0160726 A1 | 6/2010 | Windheuser | |
| 2010/0174297 A1 | 7/2010 | Speziali | |
| 2012/0157760 A1 | 6/2012 | Aklog et al. | |
| 2012/0290077 A1 | 11/2012 | Aklog et al. | |
| 2014/0039324 A1 | 2/2014 | Speziali | |

FOREIGN PATENT DOCUMENTS

| | | |
|---|---|---|
| EP | 1637091 | 3/2006 |
| EP | 1408850 B1 | 9/2009 |
| EP | 1845861 | 11/2009 |
| JP | 06142114 | 5/1994 |
| WO | WO 99/00059 | 1/1999 |
| WO | WO 99/30647 A1 | 6/1999 |
| WO | WO 00/06026 A2 | 2/2000 |
| WO | WO 00/06026 A3 | 2/2000 |
| WO | WO 00/06027 | 2/2000 |
| WO | WO 00/06028 | 2/2000 |
| WO | WO 00/16700 | 3/2000 |
| WO | WO 01/66018 | 9/2001 |
| WO | WO 01/095809 | 12/2001 |
| WO | WO 03/001893 | 1/2003 |
| WO | WO 03/059209 A2 | 7/2003 |
| WO | WO 03/082157 | 10/2003 |
| WO | WO 03/082158 | 10/2003 |
| WO | WO 04/021893 A2 | 3/2004 |
| WO | WO 04/043265 A2 | 5/2004 |
| WO | WO 05/039428 A2 | 5/2005 |
| WO | WO 05/094525 A2 | 10/2005 |
| WO | WO 06/012750 | 2/2006 |
| WO | WO 06/032051 A2 | 3/2006 |
| WO | WO 06/065966 A2 | 6/2006 |
| WO | WO 06/078694 A2 | 7/2006 |
| WO | WO 06/116310 A2 | 11/2006 |
| WO | WO 06/127509 A2 | 11/2006 |
| WO | WO 07/002627 A1 | 1/2007 |
| WO | WO 07/027451 A2 | 3/2007 |
| WO | WO 07/062128 A2 | 5/2007 |
| WO | WO 07/081418 A1 | 7/2007 |
| WO | WO 07/117612 A1 | 10/2007 |
| WO | WO 08/010738 A2 | 1/2008 |
| WO | WO 2008/112237 A2 | 9/2008 |
| WO | WO 09/052528 A2 | 4/2009 |

OTHER PUBLICATIONS

European Search Report, EP Application No. 08839048.9, dated Sep. 16, 2010, 7 pages.

Written Opinion of the International Search Authority, International Application No. PCT/US2008/080560, Filed Oct. 20, 2008, Date of Completion: Aug. 24, 2009.

Port Access System for Mitral Valve Repair Proves Its Value in Study; MedGadget, Jul. 9, 2009 as available at: http://medgadget.com/archives/2009/07port access system for mitral valve repair proves its value in study.html (5 pages).

Interactive CardioVasular and Thoracic Surgery; Abstracts: Supplemental 3 to vol. 7 (Sep. 2008), 52 pages.

Application and File History for U.S. Appl. No. 11/813,695, filed Jul. 11, 2007, Inventor: Giovanni Speziali.

Application and File History for U.S. Appl. No. 12/254,808, filed Oct. 20, 2008, Inventor: John Zentgraf.

Application and File History for U.S. Appl. No. 12/709,220, filed Feb. 19, 2010, Inventor: Giovanni Speziali.

International Search Report, Application No. PCT/US2008/080560, dated Aug. 25, 2009, 3 pages.

International Search Report, Application No. PCT/US2008/080560, dated Aug. 28, 2009, 2 pages.

Application and File History for U.S. Appl. No. 12/254,807, filed Oct. 20, 2008, Inventor: John Zentgraf.

Extended European Search Report, Application No. EP 06718728.6, dated Nov. 11, 2009.

PCT Search Report and Written Opinion, Application No. PCT/US06/01699, dated May 6, 2008.

Application and File History for U.S. Appl. No. 13/339,865, filed Dec. 29, 2011, Inventors: Zentgraf et al.

Notification of International Search Report and Written Opinion of the International Searching Authority, Application No. PCT/US2011/067884, dated Jul. 30, 2012, 8 pages.

International Preliminary Report on Patentability, Application No. PCT/US2011/067884, dated Jul. 11, 2013, 5 pages.

PCT International Preliminary Report on Patentability for PCT/US2008/080560, dated Apr. 29, 2010, 7 pages.

Application and File History for U.S. Appl. No. 13/898,709, filed May 21, 2013. Inventors: Speziali.

Application and File History for U.S. Appl. No. 13/339,865, filed Dec. 29, 2011. Inventors: Zentgraf et al.

European Search Report, EP 11863521.8, dated Nov. 15, 2015, 10 pages.

\* cited by examiner

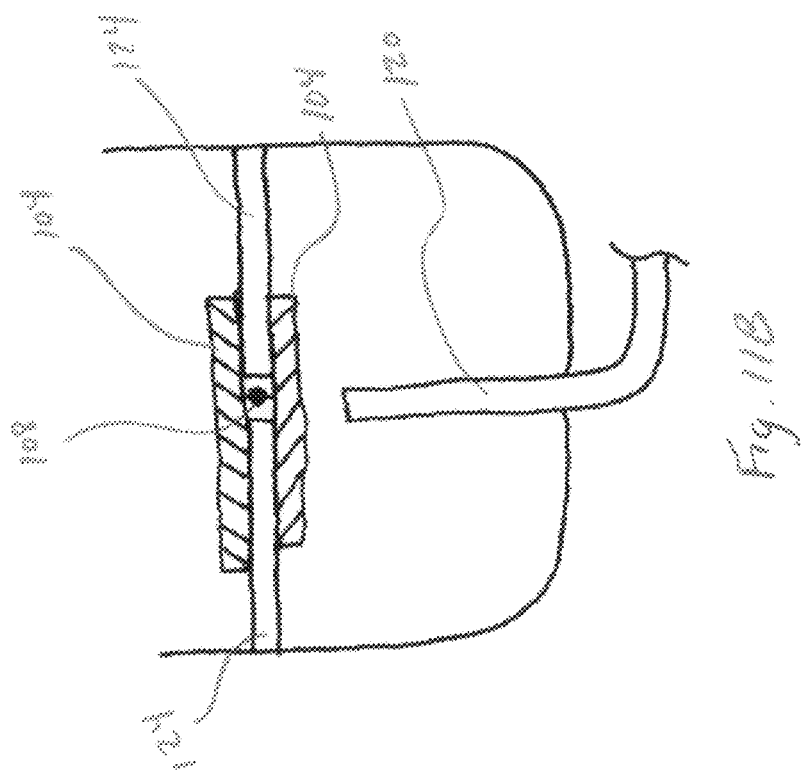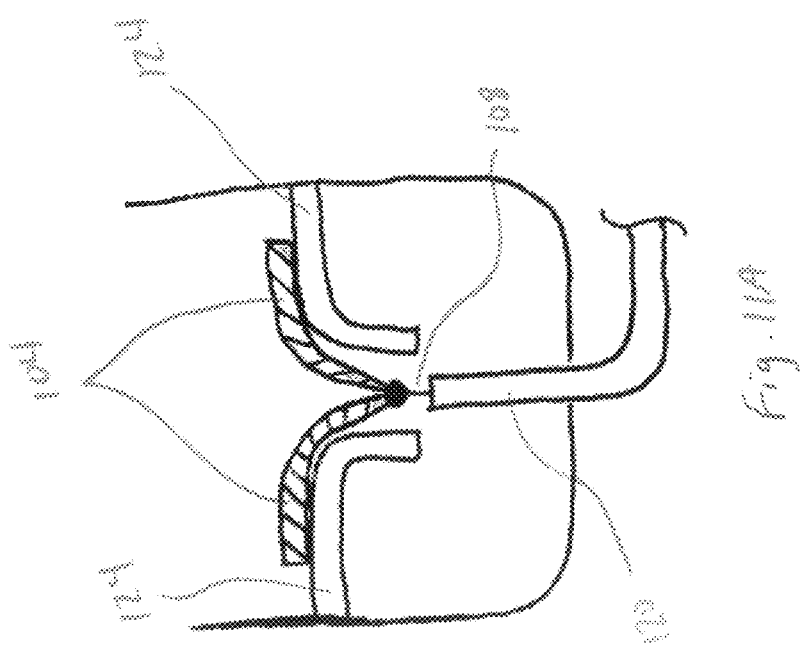

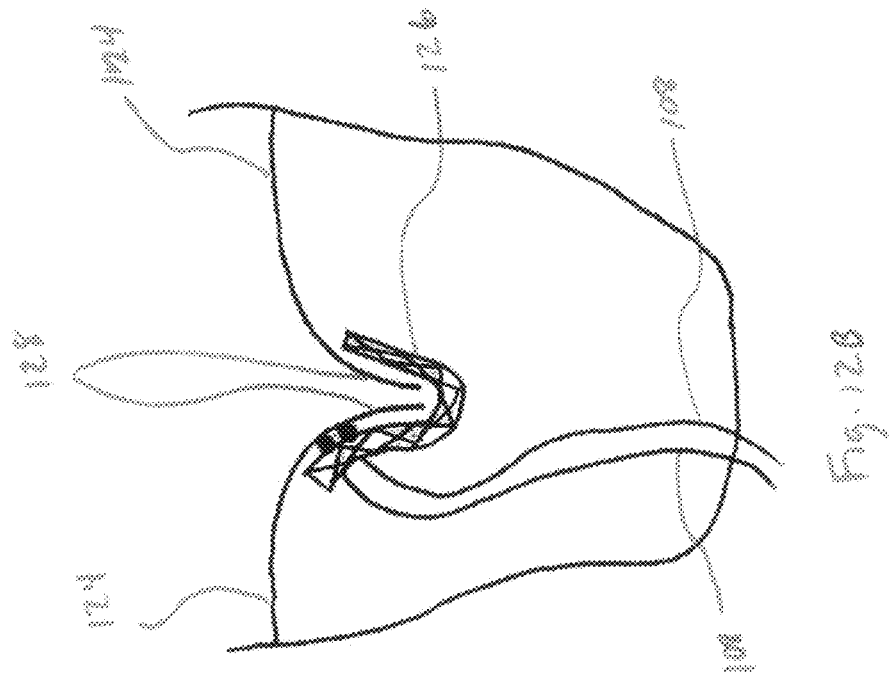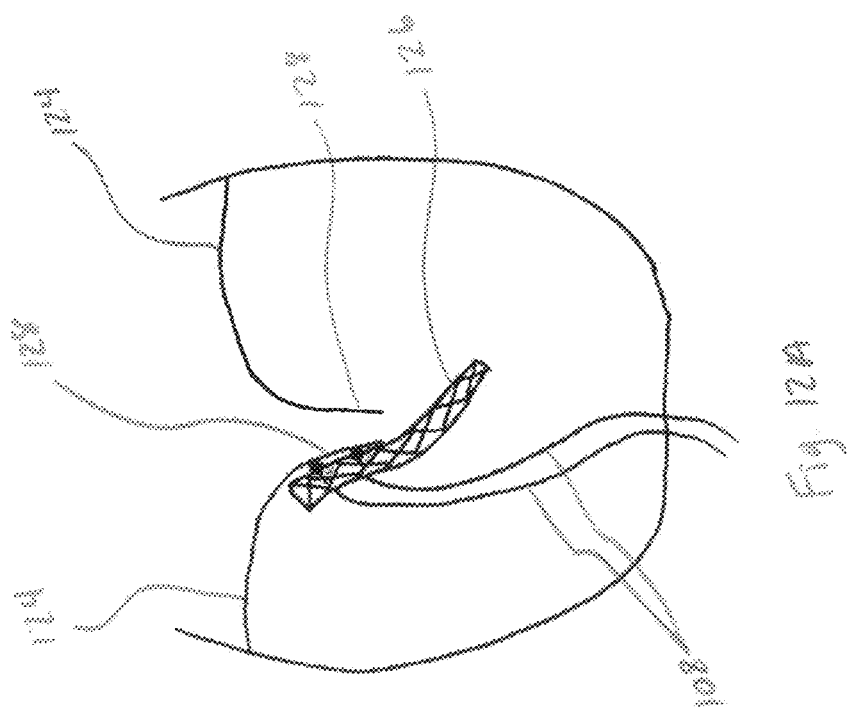

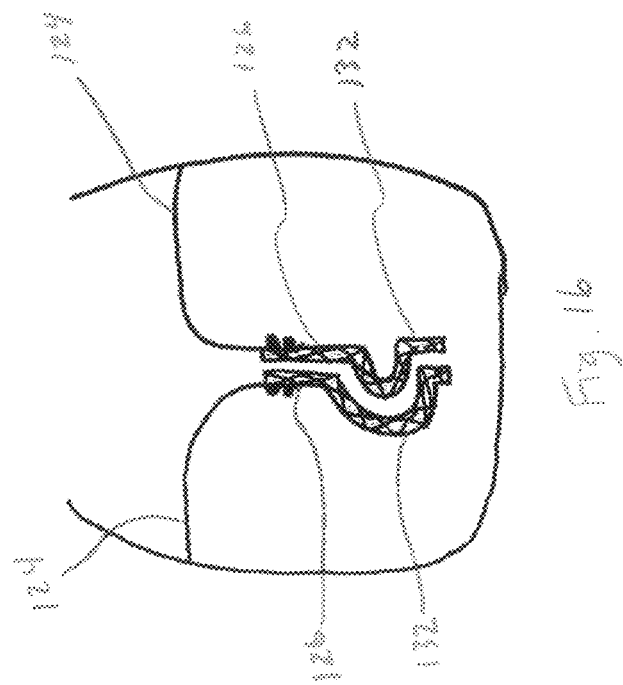
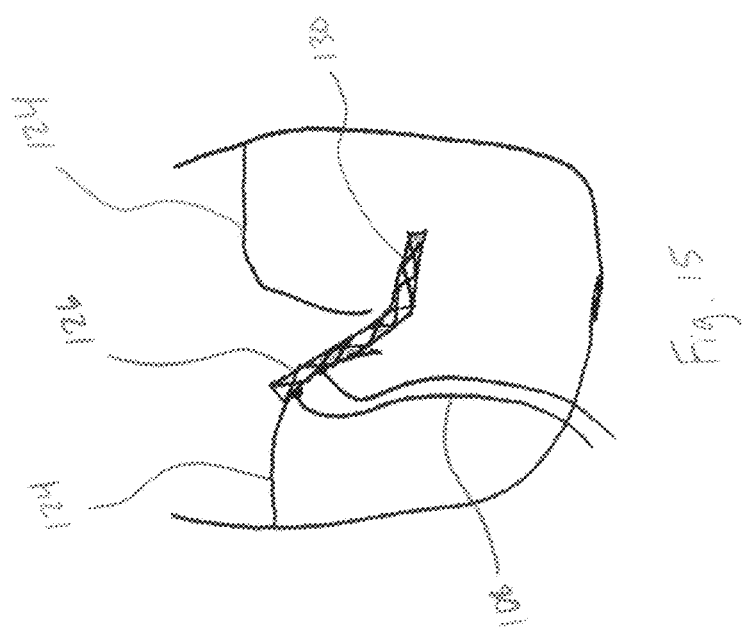

DEVICES AND METHODS FOR MINIMALLY INVASIVE REPAIR OF HEART VALVES

RELATED APPLICATION

The present application claims the benefit of U.S. Provisional Application No. 61/428,048 filed Dec. 29, 2010, which is incorporated herein in its entirety by reference.

FIELD OF THE INVENTION

The present invention relates to minimally invasive repair of a heart valve. More particularly, the present invention relates to devices for insertion into a heart valve to repair the heart valve in a beating heart of a patient.

BACKGROUND OF THE INVENTION

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a great vessel.

Using current techniques, many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood.

Of particular interest are intracardiac procedures for surgical treatment of heart valves, especially the mitral and aortic valves. According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced by excising the valve leaflets of the natural valve and securing a replacement valve in the valve position, usually by suturing the replacement valve to the natural valve annulus. Various types of replacement valves are in current use, including mechanical and biological prostheses, homografts, and allografts.

The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into a position accessible through the sternotomy. An opening, or atriotomy, is then made in the left atrium, anterior to the right pulmonary veins. The atriotomy is retracted by means of sutures or a retraction device, exposing the mitral valve directly posterior to the atriotomy. One of the aforementioned techniques may then be used to repair or replace the valve.

An alternative technique for mitral valve access may be used when a median sternotomy and/or rotational manipulation of the heart are/is undesirable. In this technique, a large incision is made in the right lateral side of the chest, usually in the region of the fifth intercostal space. One or more ribs may be removed from the patient, and other ribs near the incision are retracted outward to create a large opening onto the thoracic cavity. The left atrium is then exposed on the posterior side of the heart, and an atriotomy is formed in the wall of the left atrium, through which the mitral valve may be accessed for repair or replacement.

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae result in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle. This operation is generally carried out through a median sternotomy and requires cardiopulmonary bypass with aortic cross-clamp and cardioplegic arrest of the heart.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

One alternative to open heart surgery is a robotically guided, thoracoscopically assisted cardiotomy procedure marketed under the tradename of the DaVinci® system. Instead of requiring a sternotomy, the DaVinci® system uses a minimally invasive approach guided by camera visualization and robotic techniques. Unfortunately, the DaVinci® system is not approved for mitral valve repair procedures on a beating heart. Thus, the use of the DaVinci® system for mitral valve repair still requires a cardiopulmonary bypass with aortic cross-clamp and cardioplegic arrest of the heart.

While there are other laparoscopic and minimally invasive surgical techniques and tools that have been developed, most of these devices are not useable for the unique requirements of mitral valve repair on a beating heart. Suturing devices like the Superstich™ vascular suturing device or the Gore® suture passer are designed to permit manual placement of sutures as part of a surgical procedure, but are not designed for use on a beating heart. While certain annuloplasty techniques and instruments that can suture an annuloplasty ring as part of vascular repair or heart bypass surgery may be used in conjunction with a beating heart, these annuloplasty procedures do not involve the capture or retention of a constantly moving leaflet. Consequently, the design and use of annuloplasty techniques and instruments are of little help in solving the problems of developing instruments and techniques for minimally invasive thoracoscopic repair of heart valves.

Recently, a technique has been developed for minimally invasive thoracoscopic repair of heart valves while the heart is still beating. PCT Pub. No. WO 2006/078694 A2 to Speziali discloses a thoracoscopic heart valve repair method and apparatus. Instead of requiring open heart surgery on a stopped heart, the thorascopic heart valve repair methods and apparatus taught by Speziali utilize fiber optic technology in conjunction with transesophageal echocardiography (TEE) as a visualization technique during a minimally invasive surgical procedure that can be utilized on a beating heart. U.S. Publication No. 2008/0228223 to Alkhatib also discloses a similar apparatus for attaching a prosthetic tether between a leaflet of a patient's heart valve and another portion of the patient's heart to help prevent prolapse of the leaflet and/or to otherwise improve leaflet function.

More recent versions of these techniques are disclosed in U.S. Patent Application Publication Nos. 2009/0105751 and 2009/0105729 to Zentgraf, which disclose an integrated device that can enter the heart chamber, navigate to the leaflet, capture the leaflet, confirm proper capture, and deliver a suture as part of a mitral valve regurgitation (MR) repair.

While the Speziali and Zentgraf techniques represent a significant advance over open heart techniques and previous minimally invasive techniques for heart valve repair, it would be advantageous to further improve upon these techniques.

SUMMARY OF THE INVENTION

Methods and apparatus for heart valve repair utilize a heart valve repair device including a generally annular ring-like structure and a net structure. The ring-like structure is seated in the valve annulus with the net structure extending from the ring-like structure through the coaptation zone between leaflets. The net structure can then be anchored to a heart structure with a suture. Net structure extending between leaflets helps prevent prolapse of leaflets and can aid in coaptation.

A method of repairing a heart valve includes seating a generally annular, ring-like structure in the valve annulus above the valve leaflets. A net structure attached to the ring-like structure is extended through the coaptation zone defined between the leaflets. The net structure can be anchored to a heart structure with at least one suture.

A system for use in repairing a heart valve includes a generally annular ring-like structure, a net structure and at least one suture. The ring-like structure is dimensioned to be seated in the annulus of the valve above a pair of leaflets in the valve. The net structure is attached to the ring-like structure such that it extends through the coaptation zone between the valve leaflets when the ring-like structure is seated in the annulus. The at least one suture can extend from the net structure to anchor the net structure to another heart structure.

In another embodiment, a heart valve repair device comprises a wire form. Wire form can be comprised of a plurality of wire loops and can be deployed around a leaflet to provide a structurally supportive scaffold. Wire form can clip or clamp to both sides of the leaflet and be secured by either compression from the wire or with alternative fasteners such as a suture. Wire form can have a rigid, pre-formed shape designed to prevent prolapse.

In a further embodiment a repair device comprises one or more annular rings. Rings can be deployed around leaflets providing a physical stop preventing prolapse. Rings can clip or clamp to both sides of the leaflet. Top ring and bottom ring can be independently attached to the leaflets or connected to each other through the leaflets or coaptation zone. In one embodiment, a ring can include spokes to provide further physical barrier against prolapse.

In another embodiment, a repair device can comprise a leaflet extension comprising a pliable material shaped to conform to valve anatomy. Sutures can be used to secure a leaflet extension to a leaflet. Leaflet extension can overlap the orifice between the leaflets such that when the valve closes, the extension completes closure by overlapping any prolapsing areas of the valve.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE FIGURES

The invention may be more completely understood in consideration of the following detailed description of various embodiments of the invention in connection with the accompanying drawings, in which:

FIG. 11A is a schematic representation of a heart valve repair device implanted in a patient according to an embodiment of the present invention.

FIG. 11B is a schematic representation of the heart valve repair device of FIG. 11A implanted in a patient.

FIG. 12A is a schematic representation of a heart valve repair device implanted in a patient according to an embodiment of the present invention.

FIG. 12B is a schematic representation of the heart valve repair device of FIG. 12A implanted in a patient.

FIG. 15 is a schematic representation of a heart valve repair device implanted in a patient according to an embodiment of the present invention.

FIG. 16 is a schematic representation of a heart valve repair device implanted in a patient according to an embodiment of the present invention.

Figure 1A:
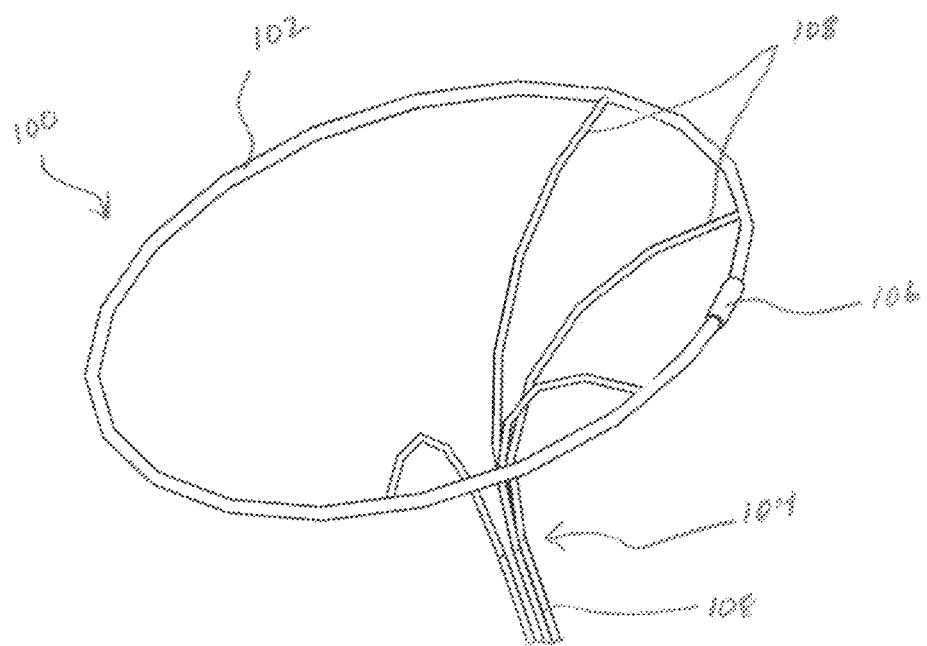
FIG. 1A is a partial perspective view of a heart valve repair device according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention.

Valve repair devices 100 according to various embodiments of the present invention are depicted in FIGS. 1A-3C. Repair devices 100 can be implanted above a heart valve in the valve annulus to help prevent prolapse of the valve leaflets. Repair devices 100 can generally include an annular ring 102 and an attachment structure 104 that extends through the valve and is anchored to a heart structure. In one embodiment, the valve to be repaired is the mitral valve. In other embodiments, other valves can be repaired, such as the tricuspid or aortic valves. In an alternative embodiment, a replacement valve can be mounted on the ring 102 for valve replacement.

Figure 1B:
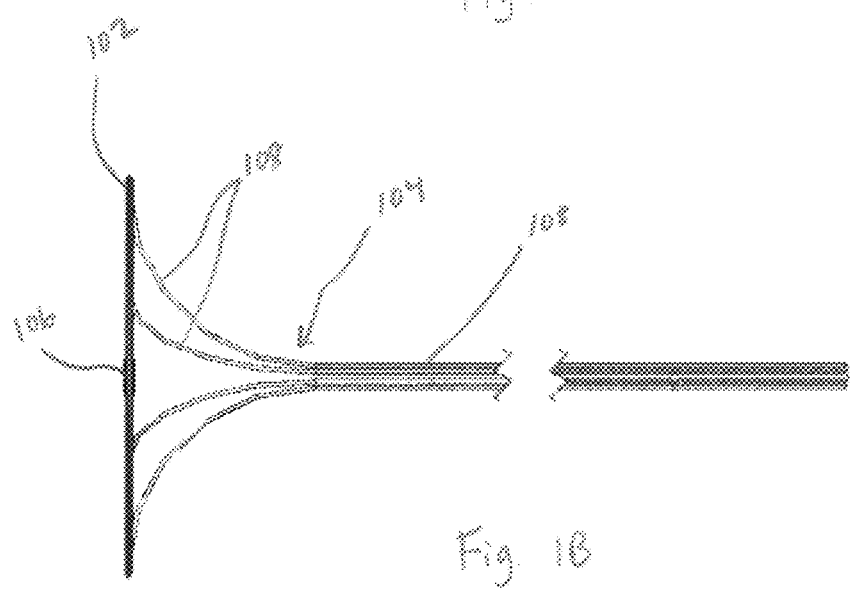
FIG. 1B is a partial side view of the heart valve repair device of FIG. 1A.

FIGS. 1A-1B depict an annular ring 102 configured as a wire form connected with a radiopaque crimp tube 106. Ring 102 can be formed of a bare metal structure, such as, for example, nitinol or stainless steel. Alternatively, ring 102 can be comprised of a metal or polymer body covered with a fabric material, such as, for example, Teflon or Dacron. In a further embodiment, ring 102 can be formed of a metal backbone with a polymer cover or coating.

Figure 2A:
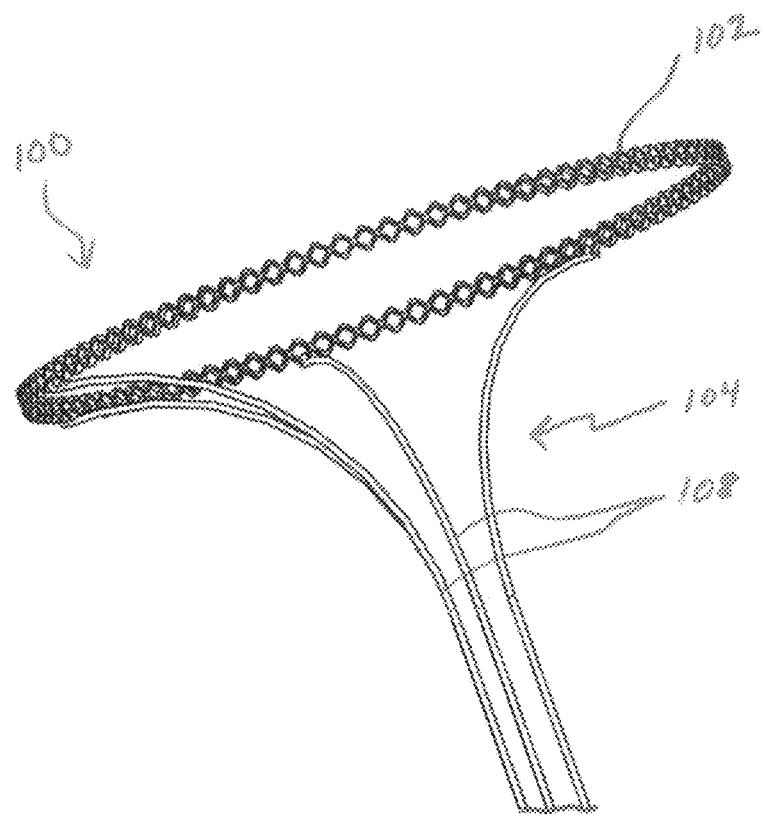
FIG. 2A is a partial perspective view of a heart valve repair device according to an embodiment of the present invention.
Figure 2B:
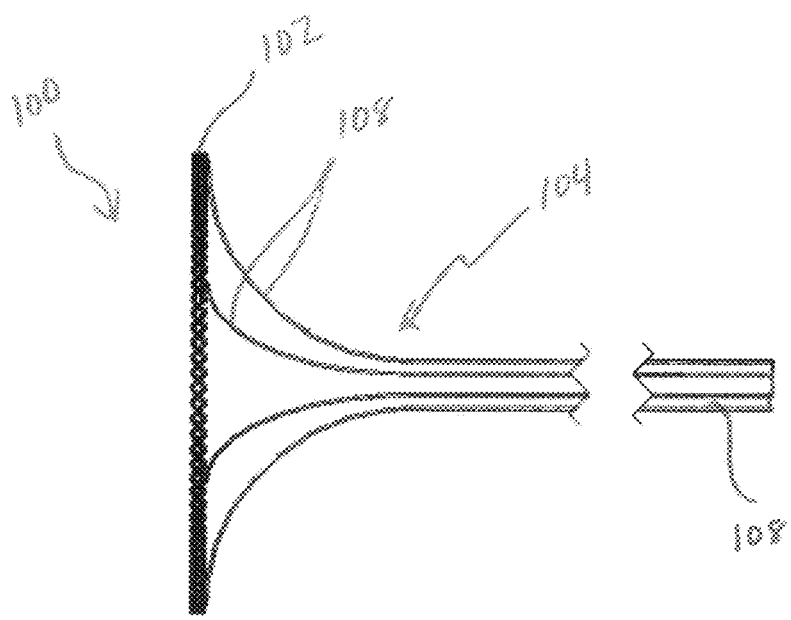
FIG. 2B is a partial side view of the heart valve repair device of FIG. 2A.
Figure 3A:
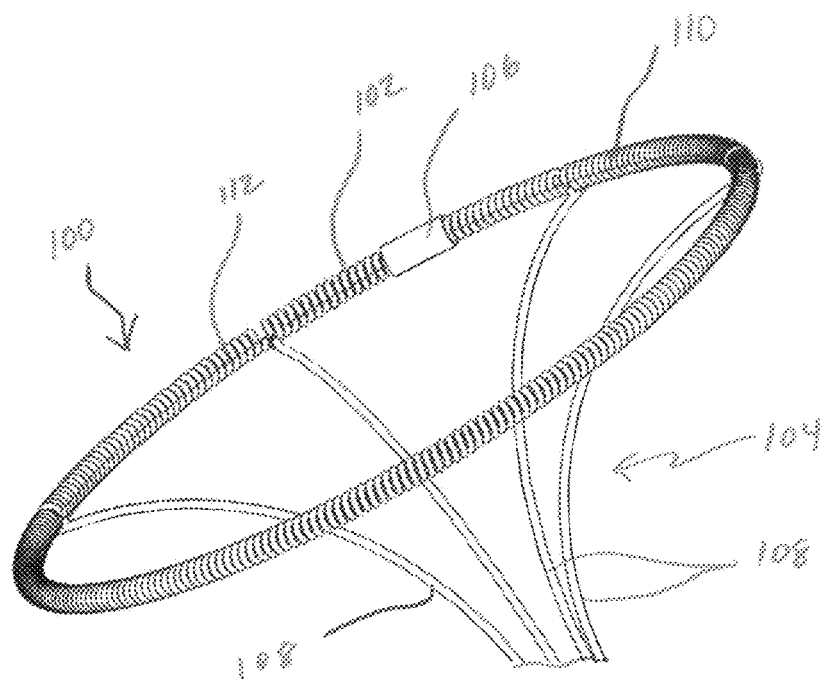
FIG. 3A is a partial perspective view of a heart valve repair device according to an embodiment of the present invention.
Figure 3B:
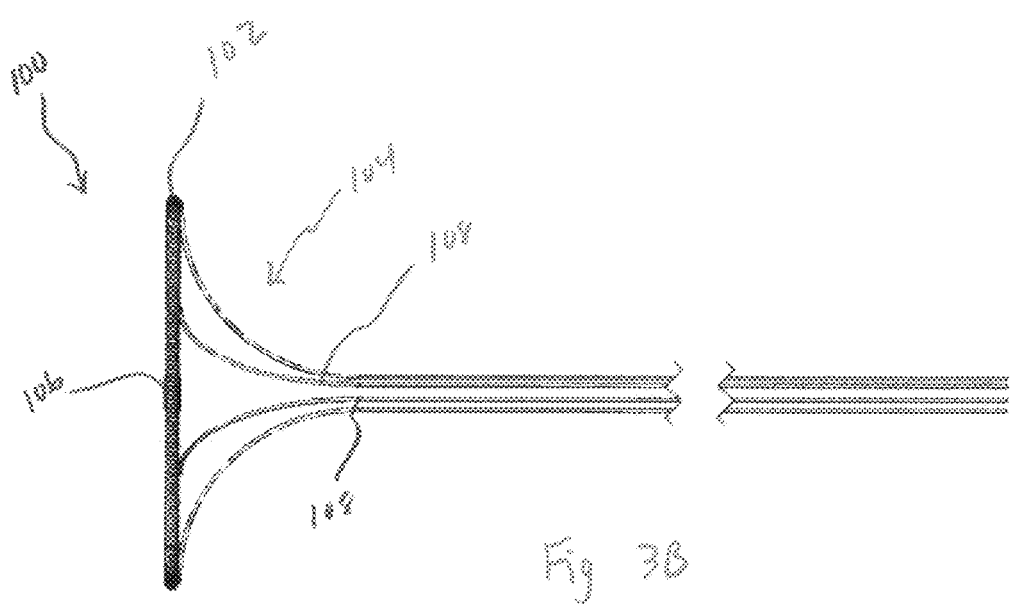
FIG. 3B is a partial side view of the heart valve repair device of FIG. 3A.

Annular ring 102 in FIGS. 2A-2B is a wire form comprising an expanded stent-like structure that can be formed from a round, rectangular or laser-cut tube segment. Such a configuration can enhance anchoring of the ring 102 in the annulus due to an outward spring force provided by the structure. Ring 102 can also be formed of a wave-like structure to allow for easier folding for delivery and repositioning. FIGS. 3A-3B include an annular ring 102 made from a coil held together with a crimp tube 106. Ring can include an outer coil structure 110 around a core wire 112, which improves the collapsed profile of the ring and lessens the pressure erosion profile. In one embodiment, coil is comprised of nitinol.

Figure 4:
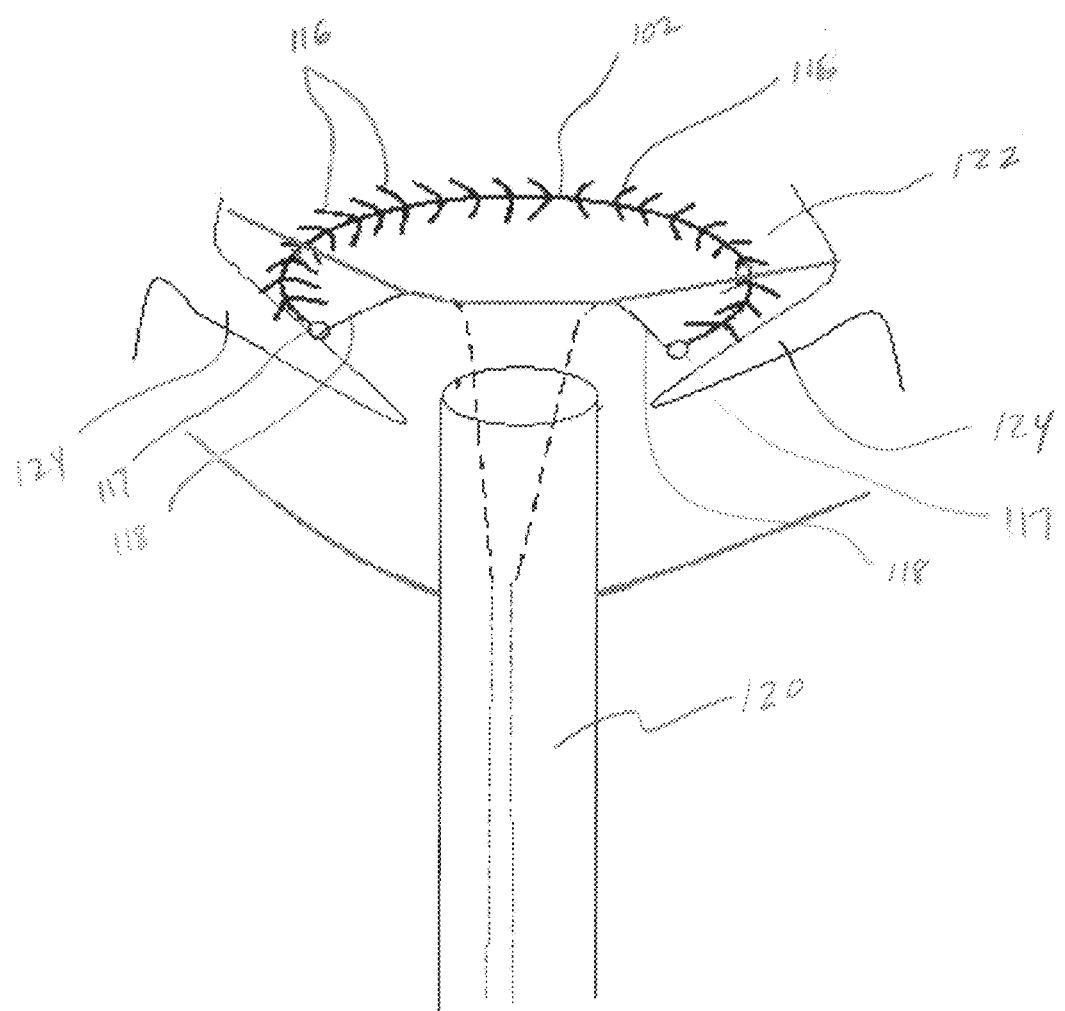
FIG. 4 is a schematic representation of a heart valve repair device being implanted in a patient according to an embodiment of the present invention.
Figure 5:
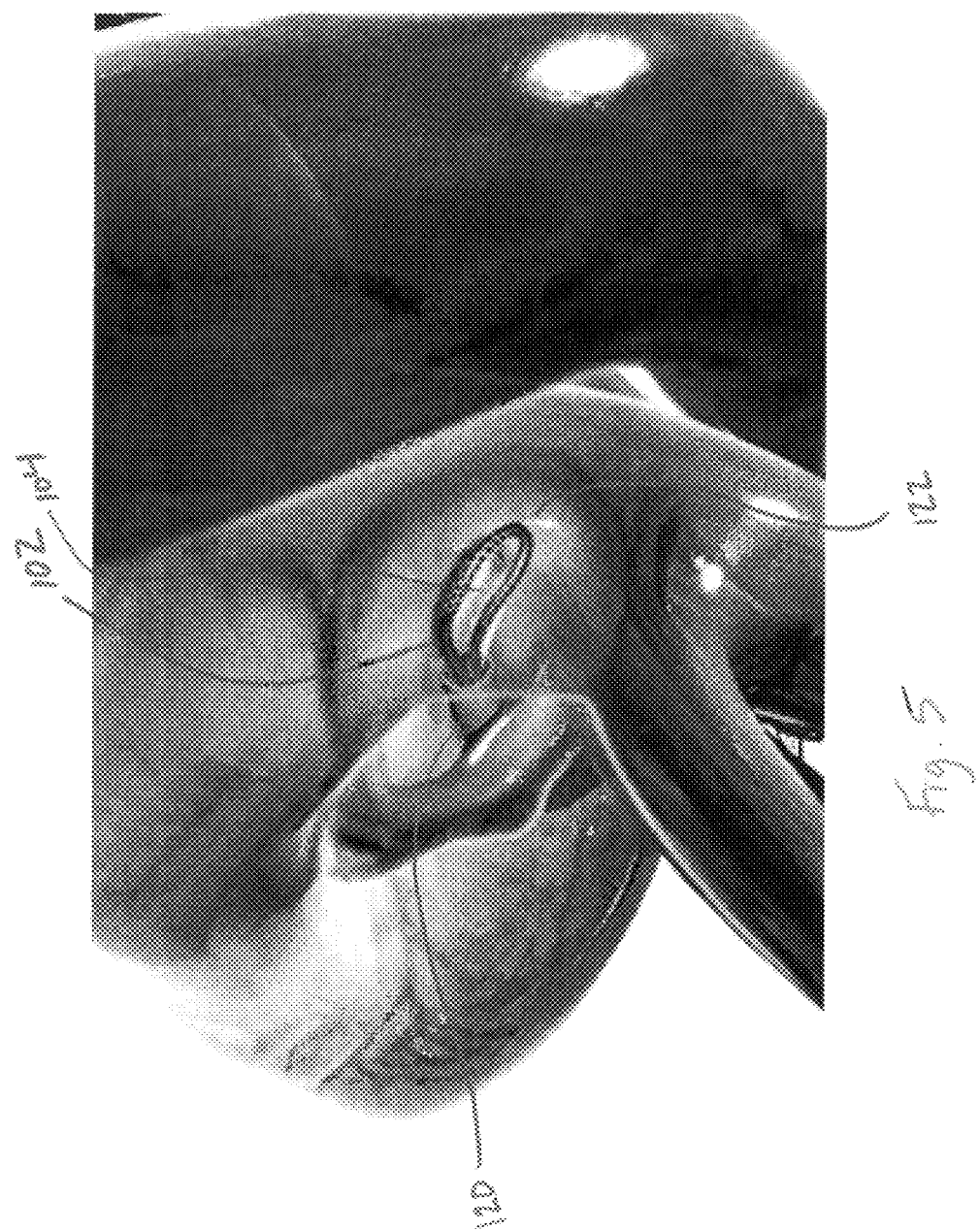
FIG. 5 is a schematic representation of a heart valve repair device being implanted in a patient according to an embodiment of the present invention.

Annular ring 102 can be a full ring (e.g., 360 degrees) or a partial ring, such as, for example, a generally C-shaped ring. In some embodiments, ring 102 can have a flat, planar profile. In other embodiments, ring 102 can have a saddle-like configuration. In one embodiment, ring 102 is secured in the annulus by hooks 116 (see FIG. 4) that extend from the ring 102 and into the annulus. In another embodiment, the ring 102 is secured in the annulus via an outwardly extending spring force generated by the mechanical properties of the ring 102. Ring 102 can function to reshape the annulus for better physiologic performance via the spring force. In one embodiment, the ring (or a separate spring) can be deployed to spread apart the commisures of the valve, which makes the annular shape more oblong to bring the leaflets closer together, thereby increasing coaption. In some embodiments, the ring 102 can be under sized to encourage diameter reduction of the valve. The shape of the ring 102 can also be optimized for retrieval by providing an easily foldable structure. Such a structure can be retrieved back into a delivery catheter to allow for repositioning. In one embodiment, a ring 102 having a generally C-shaped configuration can have eyelets 117 on each end to which tethers 118 (FIG. 4) are attached to aid in retraction and repositioning.

In one embodiment, ring 102 can include features to enhance visualization under non-invasive imaging, such as, for example, Echo. Ring 102 can include Echo markers to aid in initial deployment and adjustment of the system.

Alternatively, ring 102 can include sensors, such as, for example, a magnetic sensor that operates with a guidance system to aid in deployment and adjustment of the system.

Attachment structure can extend through the coaptation zone and function to connect the ring to a structure in the heart, such as the apex of the heart, or as an attachment point for anchoring the system to the heart. In one embodiment shown in FIGS. 1A-3C, the attachment structure 104 can comprise a plurality of sutures 108 or neochords. Sutures 108 can extend from the ring 102 through the coaptation zone of the valve leaflets and be anchored to a heart structure, such as the heart wall or papillary muscle. Multiple chords can be joined together at a natural attachment position. In another embodiment, chords extend independently from the ring to the apex or other anchor location and can therefore be individually adjusted (vector spacing). In one embodiment, the sutures/chords can be tensioned to close the circumference of the valve annulus.

Figure 7:
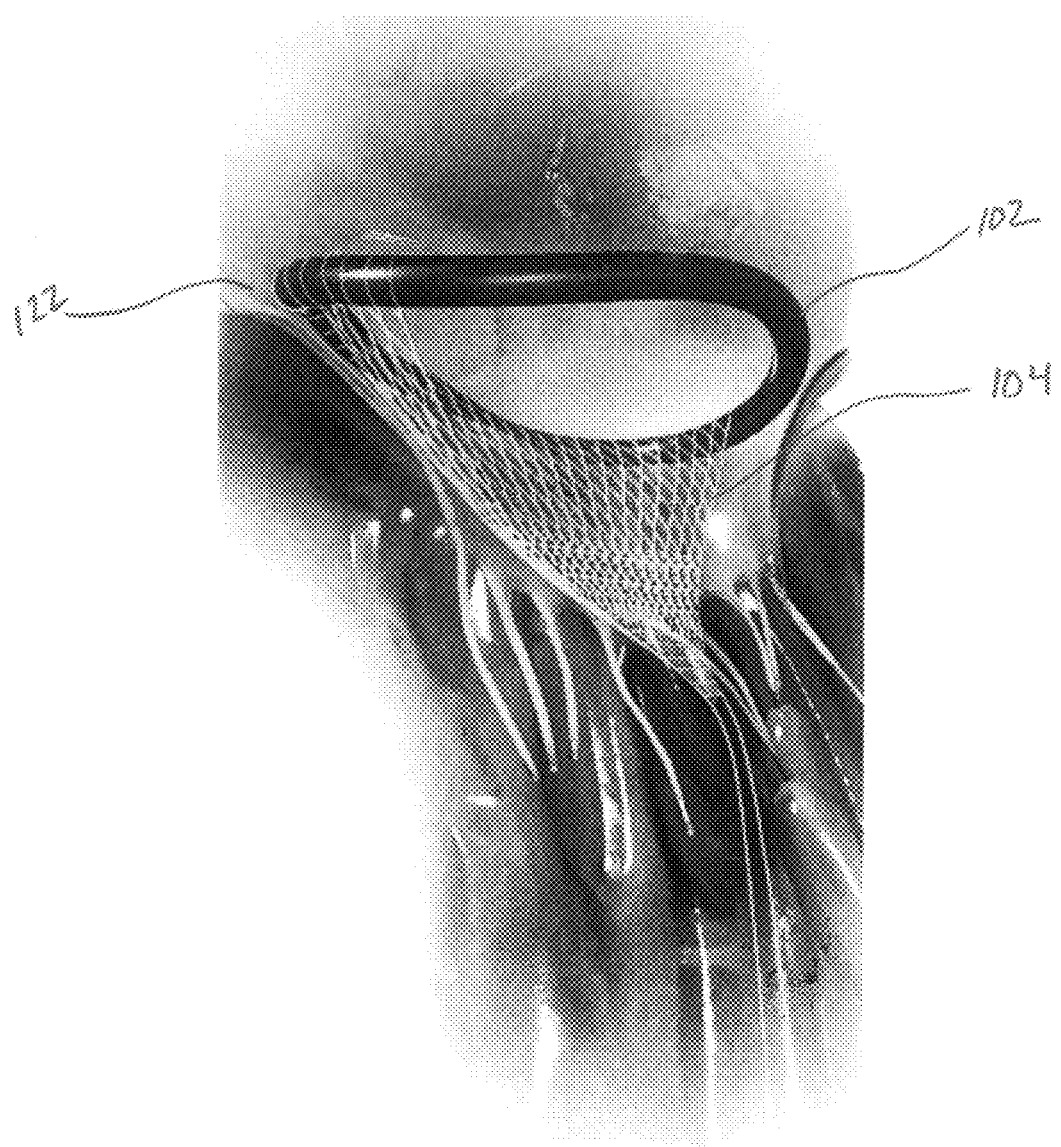
FIG. 7 is a schematic representation of a heart valve repair device implanted in a patient according to an embodiment of the present invention.
Figure 7B:
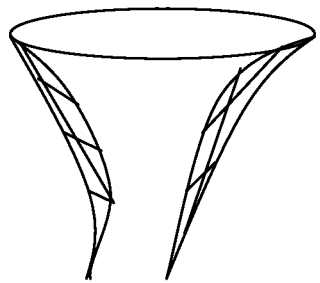
FIG. 7B is a schematic representation of a heart valve repair device according to an embodiment of the present invention with a ring carrying a plurality of partial net segments.

The attachment structure 104 can also comprise a net or a mesh or fabric structure. Net structure 104 can be threaded onto the ring 102 and can extend fully or partially (see FIG. 7) around the ring 102. In one embodiment, the ring can carry a plurality of partial net segments (see FIG. 7B). Full, partial and/or multiple net structures can be adjustable around the ring. A net structure or segment comprises a plurality of individual fabric elements, such as sutures, that interconnect at regular or irregular intervals to define a lattice-like configuration. A minimum configuration to define a "net" can be thought of as an "A" shaped structure. In one embodiment, net structure can have a generally open configuration having a greater amount of open area than fabric area. In some embodiments, similar to vascular stents, the cross-member design of the net may employ designs to improve durability, adjustability to valve leaflets or for improved anchoring.

Net or mesh-like attachment structure can have variable density within the structure to provide distinct regions directed to support, flexibility, and/or tissue response characteristics. The pattern could also contain variable porosity to provide variable support as needed for the valve structure. In one embodiment, the attachment structure can be fabricated from a thin polymer sheet such as polyurethane and laser cut to form a hole pattern ranging from a generally net-like porosity to a fine mesh-like hole pattern similar to the filter membrane of a distal protection guide wire. In a further embodiment, the attachment structure can include structural supports such as metal or plastic backbone elements incorporated into a net or mesh structure. The attachment structure can also comprise a combination of any of the above configurations.

The attachment structure can be coated with or comprise biomatrix material suitable for either tissue in-growth or non-ingrowth or a combination thereof (different sections promoting in-growth or no growth depending on location). In such an embodiment, drugs can be incorporated to enhance in-growth or non-ingrowth. Areas of denser net/mesh material and/or that have biomatrix material can be located in the coaptation zone of two leaflets (or more in some cases) to enhance resistance to prolapse in this region by increasing the native valve surface area for coaptation. Biomatrix material can be integrated into the attachment structure or can be separately inserted between attachment structures.

Net-like attachment structure 104 can extend from the ring 102 situated at the valve annulus through the coaptation zone between two valve leaflets. In one embodiment, the net structure 104 can then be anchored with one or more sutures. Sutures can anchor the net structure 104 to, for example, the heart apex, papillary muscles, or other locations on the heart wall. In another embodiment, the net structure 104 can be anchored directly to a heart structure. In other embodiments, net structure, or other attachment structure, can be secured by any other means, including mechanical, biological or chemical means or a combination thereof. In a further embodiment, net structure 104 is not anchored.

As used herein, a "coaptation zone" of valve leaflets refers to an area where the valve leaflets in a properly functioning valve meet to seal the valve during systole. In one embodiment, the coaptation zone can generally be considered the surface area over which the valve leaflets contact each other. In addition, with reference to the mitral valve, the directions "top" or "above" refer to the atrial side of the valve and the directions "bottom" or "below" refer to the ventricular side of the valve.

Figure 6:
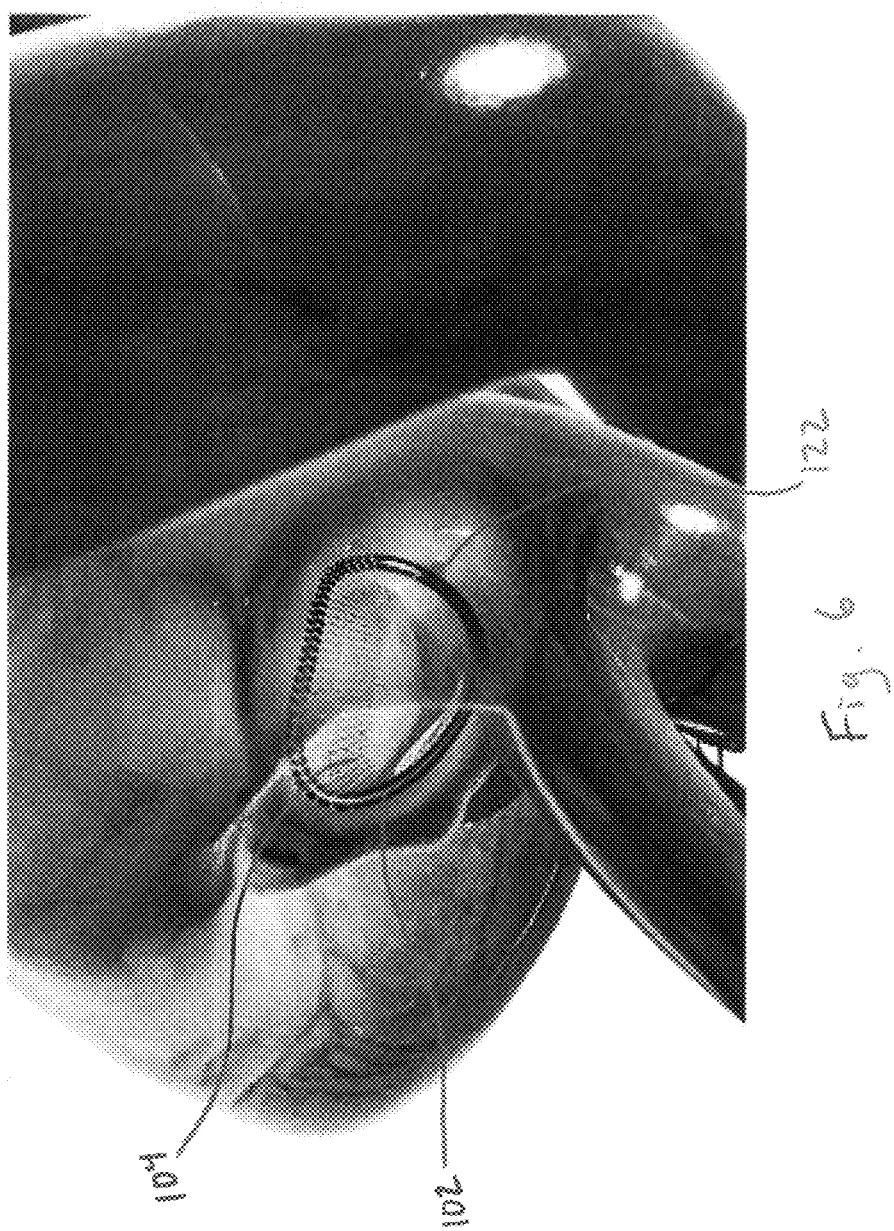
FIG. 6 is a schematic representation of a heart valve repair device implanted in a patient according to an embodiment of the present invention.

Deployment of repair device 100 can be accomplished as shown in FIGS. 4-7 with a delivery catheter 120 having the ring 102 and attachment structure 104 folded within the catheter 120. Folding for the purposes of the present invention refers to compressing the device 100 into a smaller configuration in a random fashion that may be non-uniform, similar to crumpling or wadding up a piece of paper or handkerchief. The catheter 120 is advanced into the heart chamber through a procedure such as that described in commonly owned, copending application Ser. No. 13/339, 865, which is hereby incorporated by reference, and is advanced passed the valve leaflets 124 where it is seated on the valve annulus 122 as shown in FIG. 6. The delivery catheter is then retracted, allowing the ring 102 to expand on the annulus 120. The attachment structure 104 extends through the coaptation zone between the valve leaflets and can be anchored to a heart structure as described above. The presence of the attachment structure in the coaptation zone prevents the valve leaflets from prolapsing. In one embodiment, the ring 102 is deployed with the attachment structure 104 attached to the ring 102. In another embodiment, some or all attachment structure 104 is subsequently attached to the ring 102.

In one embodiment, repair device 100 can be customized for a specific patient. In such a patient-specific embodiment, valve and heart chamber geometry for a patient can be pre-determined using pre-operative imaging. Based on the pre-operative imaging of the patient's valve, a desired ring 102 size and placement and/or quantity and configuration of attachment structure 104 such as net segments can be determined. A desired suture anchoring configuration such as number and location of sutures can also be determined. In one embodiment, the density of a net-like attachment structure 104 can be varied based on the patient's valve pathology. The ring 102, attachment structure 104 and anchoring structure can then be placed in the desired configuration with the aid of non-invasive imaging techniques and/or device-based imaging.

Figure 8B:
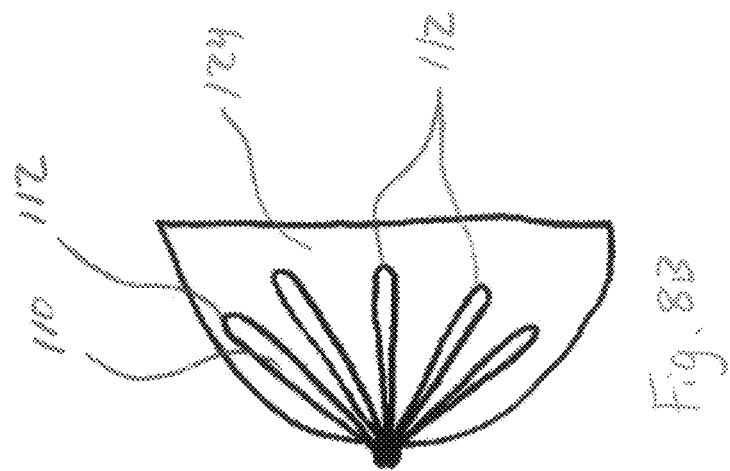
FIG. 8B is a schematic representation of the heart valve repair device of FIG. 8A implanted in a patient.
Figure 8A:
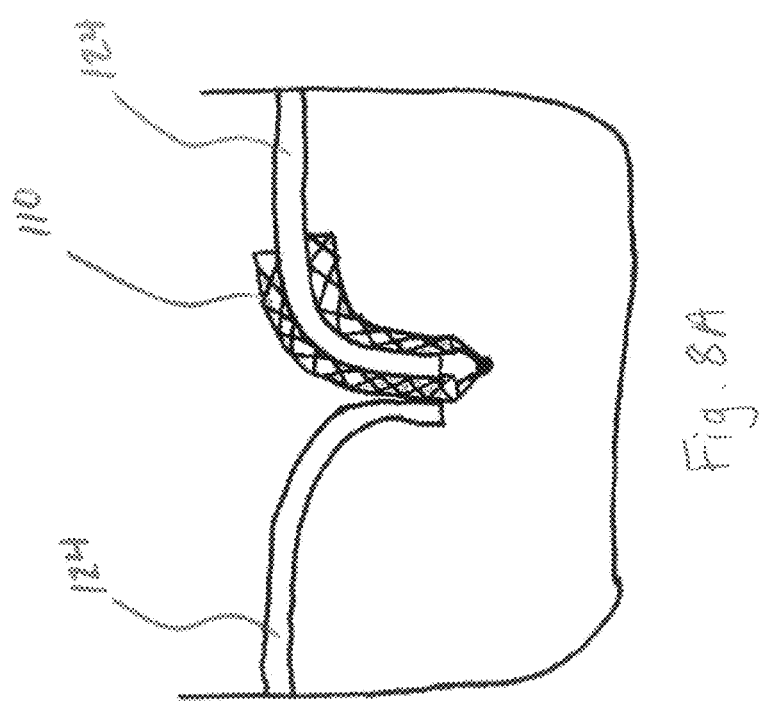
FIG. 8A is a schematic representation of a heart valve repair device implanted in a patient according to an embodiment of the present invention.
Figure 9A:
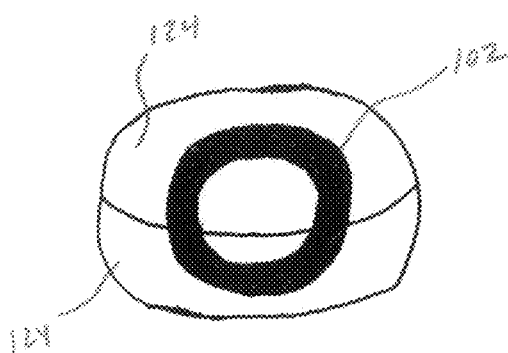
FIG. 9A is a schematic representation of a heart valve repair device implanted in a patient according to an embodiment of the present invention.
Figure 9B:
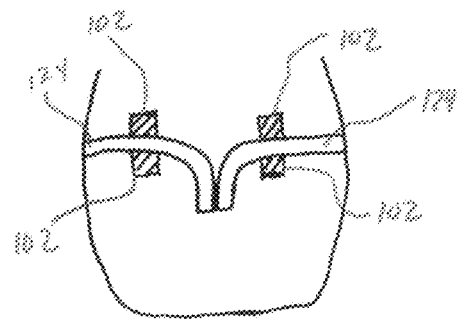
FIG. 9B is a schematic representation of the heart valve repair device of FIG. 9A implanted in a patient.

In an embodiment shown in FIGS. 8A and 8B, the repair device comprises a wire form 110 that is deployed around the leaflet 124 to provide a structurally supportive scaffold. In one embodiment, the wire form 110 is comprised of a plurality of wire loops 112. The wire form 110 can clip or clamp to both sides of the leaflet and be secured by either compression from the wire or with alternative fasteners such as a suture. The wire 110 can be deployed via a deployment catheter or advanced along a preplaced suture in a monorail/guidewire fashion. Wire form 110 can have a rigid, preformed shape designed to prevent prolapse. In addition, sutures and/or net or mesh-like attachment structures 104 can be anchored at one end to the leaflet via the wire form 110 and at the opposite end to the heart wall.

Figure 10A:
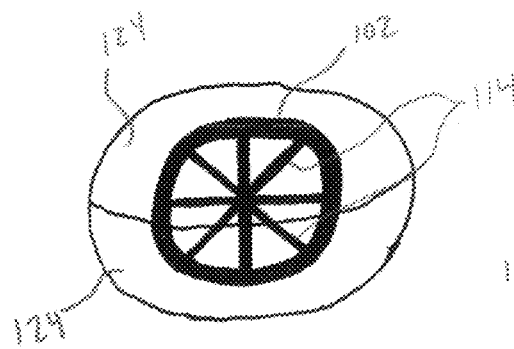
FIG. 10A is a schematic representation of a heart valve repair device implanted in a patient according to an embodiment of the present invention.
Figure 10B:
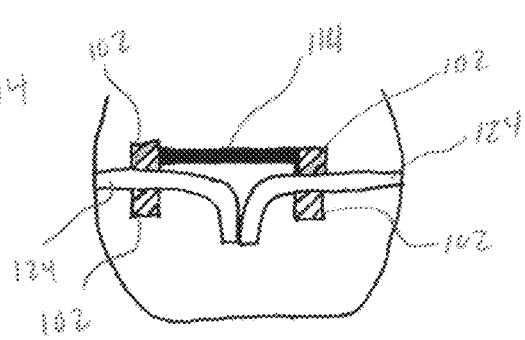
FIG. 10B is a schematic representation of the heart valve repair device of FIG. 10A implanted in a patient.

In a further embodiment depicted in FIGS. 9A-9B and 10A-10B, the repair device comprises one or more annular rings 102 that are deployed around the leaflet 124 providing a physical stop preventing prolapse. The rings 102 can clip or clamp to both sides of the leaflet 124. In one embodiment the top ring and bottom ring are independently attached to the leaflets. In another embodiment, a connecting mechanism, such as a suture 108, connects the top and bottom rings either through the coaptation zone or through the leaflets. As shown in FIGS. 10A-10B, the ring 102 can include spokes 114 to provide further physical barrier against prolapse. Alternatively, the repair device can comprise a net-like attachment structure 104 that is deployed around the leaflets. Repair device, whether ring 102 or net-like structure 104, can be deployed directly around the leaflets via a deployment catheter 120 as shown in FIGS. 11A-11B or can be advanced along a preplaced suture in a monorail/guidewire fashion.

In certain embodiments, any repair device according to the present invention can be delivered using a suture as a guidewire. A suture can first be delivered into the heart via a deployment catheter and anchored to a valve leaflet. The suture can then be used as a guidewire such that the repair device is advanced along the suture to the leaflet. The suture can subsequently be anchored to another heart structure or removed after the repair device has been delivered.

In another embodiment, independent catheters are utilized to deploy a valve repair device that comprises a helical structure that is deployed retrograde from the heart chamber apex to a position on the opposite side of the valve with the helix fixed at the heart chamber apex. During systolic contraction of the heart and valve closure, the flail segment of any leaflet would be brought into coaptation by the compression of the helical device above the plane of the valve leaflets.

Referring now to FIGS. 12A-12B, a repair device can comprise a leaflet extension 126. Leaflet extension 126 can comprise a pliable material suitable as an artificial leaflet surrogate, such as, for example, bovine pericardium or CorMatrix ECM, Dacron, Teflon, polyurethane or dura matter and can be shaped to conform to valve anatomy. Sutures 108 can be used to secure a leaflet extension 126 to a leaflet 124. The leaflet extension 126 can be attached adjacent a free edge 128 of one leaflet 124. The leaflet extension 126 overlaps the orifice between the leaflets 124 such that when the valve closes, the extension 126 completes closure by overlapping any prolapsing areas of the valve. Extension 126 can be placed on either the atrial or the ventricular side of the leaflet and extend under or over an adjacent leaflet. Extensions 126 can be attached to the full length of a leaflet 124 or a partial length.

Figure 13A:
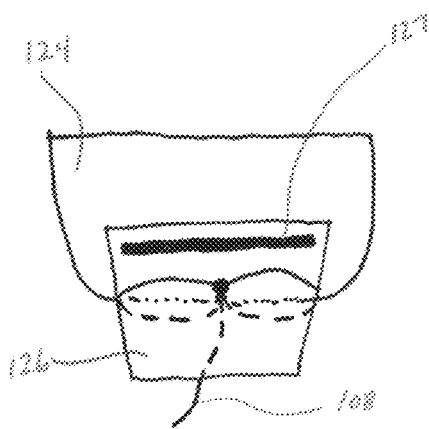
FIG. 13A is a schematic representation of a heart valve repair device implanted in a patient according to an embodiment of the present invention.
Figure 13B:
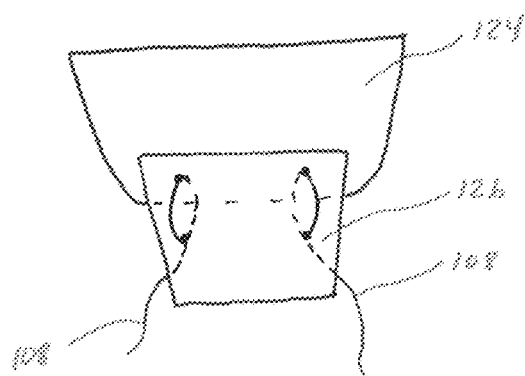
FIG. 13B is a schematic representation of a heart valve repair device implanted in a patient according to an embodiment of the present invention.
Figure 14A:
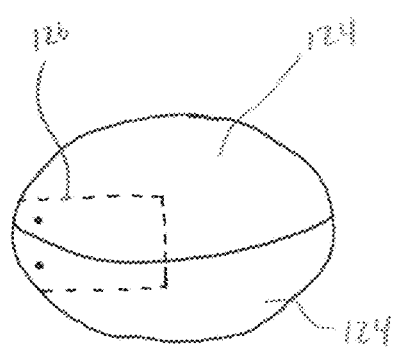
FIG. 14A is a schematic representation of a heart valve repair device implanted in a patient according to an embodiment of the present invention.
Figure 14B:
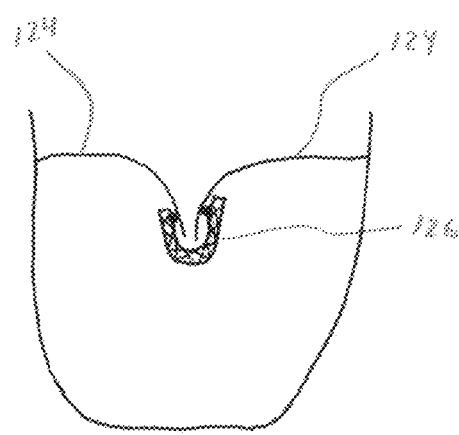
FIG. 14B is a schematic representation of the heart valve repair device of FIG. 14A implanted in a patient.

To deploy a leaflet extension 126, the leaflet 124 can be captured and a suture 108 deployed into the leaflet 124 as described in PCT Pub. No. WO 2006/078694 A2 to Speziali and U.S. Patent Application Publication Nos. 2009/0105751 and 2009/0105729 to Zentgraf, each of which is hereby incorporate by reference, and in copending application Ser. No. 13/339,865, previously incorporated herein by reference. The suture 108 can then be passed through the extension 126. A girth hitch knot can then be formed with the suture 108 as shown in FIG. 13A. Extension 126 can also be affixed to the leaflet 124 with multiple sutures 108 such as in FIG. 13B. In one embodiment, extensions 126 can have reinforced areas where the sutures are inserted. Alternatively, the extension can be attached via a non-suture method, such as, for example, clips, a clamp, adhesive or an anchor. In another embodiment shown in FIGS. 14A and 14B, a leaflet extension 126 can be attached to both leaflets 124 to span the orifice between leaflets. In one embodiment, sutures 108 through extension 126 can be tethered under minimal tension to a tissue structure (e.g. heart apex). Alternatively, extension 126 can be fixed to the leaflet 124 and excess suture 108 can be cut and removed.

In some embodiments, leaflet extension 126 can have reinforced areas 127 for exoskeletal support and/or for suture attachment. In an embodiment, shown in FIG. 15, extension 126 includes a pre-shaped feature 130 that ensures overlap under the adjacent leaflet during valve closure. FIG. 16 depicts extensions 126 having matching preshaped features 132 that ensure coaptation during valve closure. Pre-shaped features can act as an exoskeletal support, shape alteration to better match the contour of the leaflet's leading edge, or better contour to maximize coaptation length. If adhered to the leaflet, the feature can be used as a strength member to reinforce the leaflet or to alter the shape of the valve orifice geometry to better reduce regurgitation. In one embodiment, pre-shaped features can be of a shape memory material such as, for example, nitinol or thermoelastic. In one embodiment, the extension can be drug coated and have drug elution properties to optimize function, adhesion, and/or mitigate clotting risks.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A method of repairing a heart valve, the heart valve including a native valve annulus and at least a pair of native valve leaflets, comprising:

seating a generally annular, ring-like structure in the native valve annulus above the native valve leaflets;

extending a net structure across a coaptation zone defined between the native valve leaflets, the net structure consisting of a fabric-like mesh having a generally open configuration having a greater amount of uncovered open areas than fabric areas, the fabric-like mesh positioned between the native valve leaflets and over at least a portion of a top surface of at least one of the native valve leaflets defining the coaptation zone such that the net structure functions to allow the native valve leaflets to open and close while inhibiting prolapse of the native valve leaflets without promoting in-growth of leaflet tissue into the net structure, and wherein the net structure is attached to the ring-like structure with a plurality of loops, each of the loops defined by an uncovered open area of the fabric-like mesh and arranged around an outer surface of at least a portion of the ring-like structure adjacent one or more other of the loops; and anchoring the net structure at one or more locations below the native valve leaflets.

2. The method of claim 1, wherein the generally, annular ring-like structure comprises a ring.

3. The method of claim 1, wherein the generally annular ring-like structure comprises a partial ring.

4. The method of claim 1, further comprising altering the shape of the ring-like structure and net structure to fold the ring-like structure and net structure into a catheter for delivery to the valve.

5. The method of claim 1, wherein the net structure extends around only a portion of the ring-like structure.

6. The method of claim 1, wherein the fabric-like mesh defines a plurality of separate unconnected net segments separately attached to the ring-like structure.

7. The method of claim 1, wherein the step of seating a generally annular, ring-like structure in the valve annulus includes engaging a plurality of hooks on the ring-like structure with the annulus.

8. The method of claim 1, wherein the step of seating a generally annular, ring-like structure in the valve annulus including positioning the ring-like structure such that it is retained in the annulus via an outwardly extending spring force generated by the ring-like structure.

9. The method of claim 1, the step of anchoring the net structure at one or more locations below the valve leaflets includes anchoring the net structure to a heart structure with at least one suture.

10. A system for use in repairing a heart valve, comprising:
   a generally annular ring-like structure, the ring-like structure dimensioned to be seated in a native annulus of a valve above a pair of native valve leaflets in the valve that define a coaptation zone;
   an open net structure consisting of a fabric-like mesh having a greater amount of uncovered open areas than fabric areas, the fabric-like mesh threaded along an outer surface of the ring-like structure such that the uncovered open areas extend from the ring-like structure over at least a portion of a top surface of at least one of the native valve leaflets when the ring-like structure is seated in the native annulus of the valve and extend between the pair of native valve leaflets within the coaptation zone to inhibit prolapse of the native valve leaflets while otherwise enabling normal opening and closing of the native valve leaflets, wherein the net structure is not configured to promote in-growth of leaflet tissue into the net structure, and wherein the fabric-like mesh includes a plurality of loops each defined by an uncovered open area of the fabric-like mesh and arranged adjacent to one or more of the other loops around an outer surface of at least a portion of the ring-like structure; and
   at least one suture adapted to extend from the net structure to anchor the net structure below the valve leaflets.

11. The system of claim 10, wherein the generally, annular ring-like structure comprises a ring.

12. The system of claim 10, wherein the generally annular ring-like structure comprises a partial ring.

13. The system of claim 10, wherein the net structure extends around only a portion of the ring-like structure.

14. The system of claim 10, wherein the fabric-like mesh defines a plurality of separate unconnected net segments separately connected to the ring-like structure.

15. The system of claim 10, wherein the generally annular, ring-like structure includes a plurality of hooks adapted to engage the annulus to retain the ring-like structure in the annulus.

16. The system of claim 10, wherein the generally annular, ring-like structure generates an outwardly extending spring force to retain the ring-like structure in the annulus.

* * * * *

UNITED STATES PATENT AND TRADEMARK OFFICE
CERTIFICATE OF CORRECTION

PATENT NO. : 10,080,659 B1  
APPLICATION NO. : 13/340185  
DATED : September 25, 2018  
INVENTOR(S) : Zentgraf et al.

Page 1 of 1

It is certified that error appears in the above-identified patent and that said Letters Patent is hereby corrected as shown below:

On the Title Page

Item (75), Line 3, After Arun please delete "Sarini" and insert --Saini--.

Signed and Sealed this  
Seventh Day of May, 2019

Andrei Iancu  
*Director of the United States Patent and Trademark Office*